United States Patent
Yago

(10) Patent No.: US 10,427,438 B2
(45) Date of Patent: Oct. 1, 2019

(54) ABNORMALITY DETECTION AND PROCESSING FOR IMAGE FORMING SYSTEMS AND DEVICES

(71) Applicant: Konica Minolta, Inc., Chiyoda-ku, Tokyo (JP)

(72) Inventor: Hiroaki Yago, Hino (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 16/107,105

(22) Filed: Aug. 21, 2018

(65) Prior Publication Data

US 2019/0061397 A1     Feb. 28, 2019

(30) Foreign Application Priority Data

Aug. 31, 2017    (JP) ................. 2017-167073

(51) Int. Cl.
| | |
|---|---|
| *B41J 29/46* | (2006.01) |
| *G01N 21/892* | (2006.01) |
| *B41J 29/393* | (2006.01) |
| *B41J 29/38* | (2006.01) |

(52) U.S. Cl.
CPC ............... *B41J 29/46* (2013.01); *B41J 29/38* (2013.01); *B41J 29/393* (2013.01); *G01N 21/892* (2013.01)

(58) Field of Classification Search
CPC ........ B41J 29/46; B41J 29/393; G01N 21/892
See application file for complete search history.

(56) References Cited

U.S. PATENT DOCUMENTS

| | | | | |
|---|---|---|---|---|
| 5,631,747 | A * | 5/1997 | Farrell ................. | H04N 1/3873 358/401 |
| 6,975,828 | B2 * | 12/2005 | Bessho .............. | G03G 15/0152 358/450 |
| 7,336,912 | B2 * | 2/2008 | Yamauchi .............. | B26D 5/007 399/385 |
| 2002/0051139 | A1 * | 5/2002 | Akabane ................ | G06K 15/02 358/1.2 |
| 2009/0269520 | A1 * | 10/2009 | Ishii ................... | G06K 9/00442 358/1.14 |
| 2014/0300918 | A1 * | 10/2014 | Kiriyama ........... | G06K 9/00442 358/1.14 |

FOREIGN PATENT DOCUMENTS

JP      2014-178282      9/2014

* cited by examiner

*Primary Examiner* — G. M. A Hyder
(74) *Attorney, Agent, or Firm* — Baker Hostetler

(57) ABSTRACT

A control device determines whether an abnormality occurs in an image formed on a paper sheet with reference to image forming information regarding image formation generated by an image forming device that provides an area to be cut in the paper sheet and forms an image in an image forming area and read image information generated according to reading by a reading device that reads the image formed on the paper sheet, and generates control information for controlling image formation of the image forming device, wherein in a case where an abnormality is detected in the image forming area, the control device generates control information for adjusting positions of the image forming area and the area to be cut to move the abnormality to the area to be cut and notifies the image forming device of the control information.

21 Claims, 13 Drawing Sheets

FIG. 3
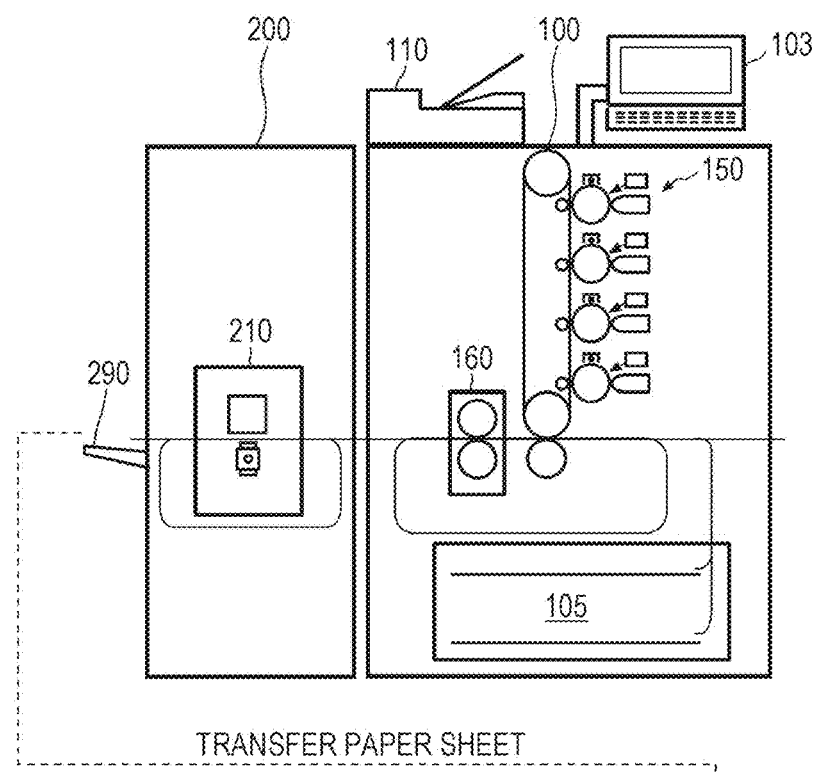
TRANSFER PAPER SHEET
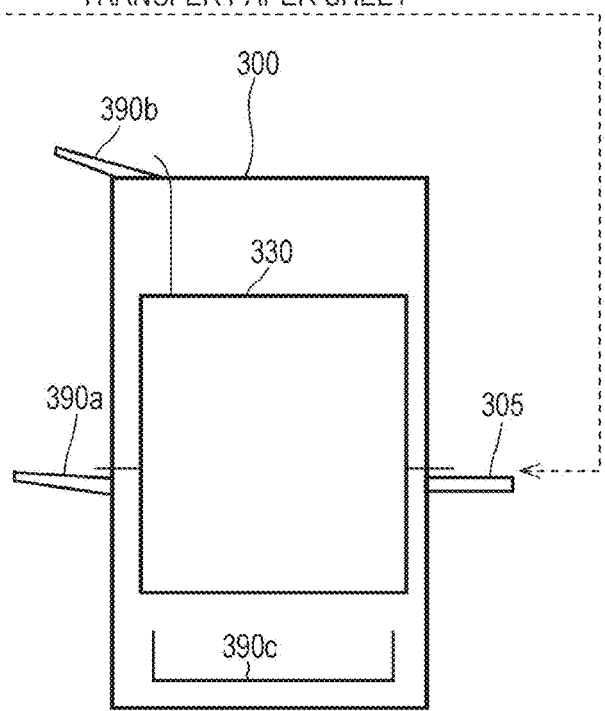

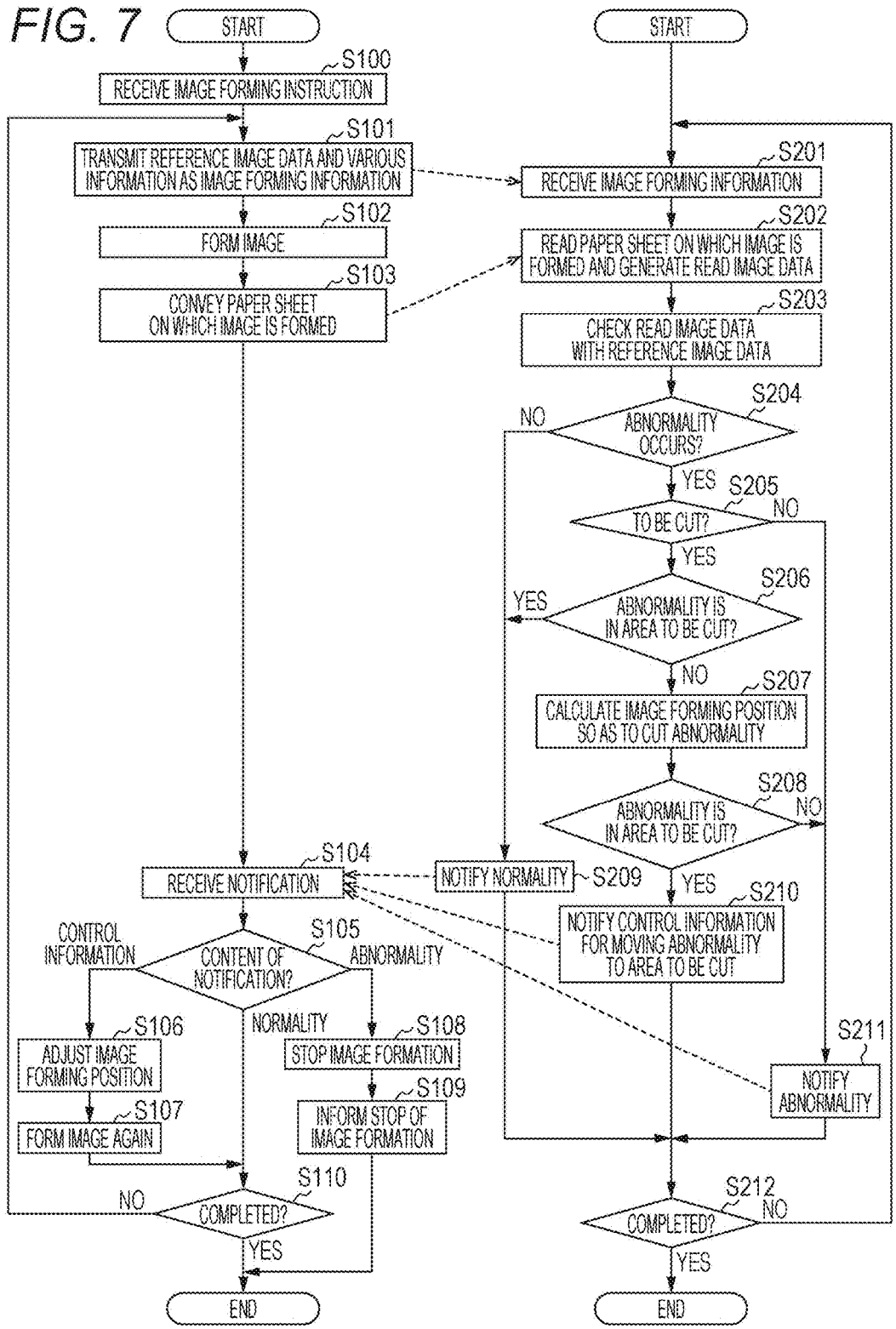

ABNORMALITY DETECTION AND PROCESSING FOR IMAGE FORMING SYSTEMS AND DEVICES

The entire disclosure of Japanese patent Application No. 2017-167073, filed on Aug. 31, 2017, is incorporated herein by reference in its entirety.

BACKGROUND

Technological Field

The present invention relates to a control device, a reading device, an image forming device, an image forming system, and a control program capable of restarting image formation while reducing downtime as small as possible in a case where a failure and an abnormality such as a contamination occurs on a paper sheet.

Description of the Related Art

In recent years, stability against printed matters has been required, and a mechanism for quickly and accurately find a failure and an abnormality of the printed matter and prevent the printed matters with the failure and the abnormality from going on the market has been required.

To cope with this situation, there is a technique for reading an image on the printed matter, comparing the read image with a reference image, and examining the image on the printed matter. Furthermore, there is a technique for automatically reprint a printed matter which has been determined to have waste through the examination.

However, at the time of reprinting, there is a case where failures continuously occur according to a kind of the failure, there has been a problem in that reprinting and the determination that the printed matter has waste are repeated and defective printed matters are continuously generated.

Regarding these problems, various proposals have been made in JP 2014-178282 A.

In JP 2014-178282 A, in consideration of a state where a defect occurs, a defect occurrence rate is calculated, a completion possibility that is a possibility in which printing processing in progress is completed within a predetermined number of times of reprinting based on the calculated defect occurrence rate, and waste paper is reduced by determining whether an image forming job is continued or stopped.

However, in the related art, priming is forced to be stopped in a case where waste continuously occurs. That is, a new problem is created such that the image formation cannot be continued and the downtime is increased.

SUMMARY

The present invention has been made in consideration of the above problems. An object of the present invention is to realize a control device, a reading device, an image forming device, an image forming system, and a control program capable of avoiding finally making a defective printed matter and preventing downtime in image formation even when a failure and abnormality on a printed matter continuously occur.

To achieve the abovementioned object, according to an aspect of the present invention, a control device reflecting one aspect of the present invention determines whether an abnormality occurs in an image formed on a paper sheet with reference to image forming information regarding image formation generated by an image forming device that provides an area to be cut in the paper sheet and forms an image in an image forming area and read image information generated according to reading by a reading device that reads the image formed on the paper sheet, and generates control information for controlling image formation of the image forming device, wherein in a case where an abnormality is detected in the image forming area, the control device generates control information for adjusting positions of the image forming area and the area to be cut to move the abnormality to the area to be cut and notifies the image forming device of the control information.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 3 is a configuration diagram illustrating a configuration according to an embodiment of the present invention;

FIG. 7 is a flowchart of an operation according to an embodiment of the present invention;

DETAILED DESCRIPTION OF EMBODIMENTS

Hereinafter, one or more embodiments of a control device, a reading device, an image forming device, an image forming system, and a control program, which are capable of avoiding finally making a defective printed matter and preventing downtime in image formation even when a failure and an abnormality on a printed matter continuously occur, of the present invention will be described with reference to the drawings. However, the scope of the invention is not limited to the disclosed embodiments.

[Configuration (1)]

Figure 1:
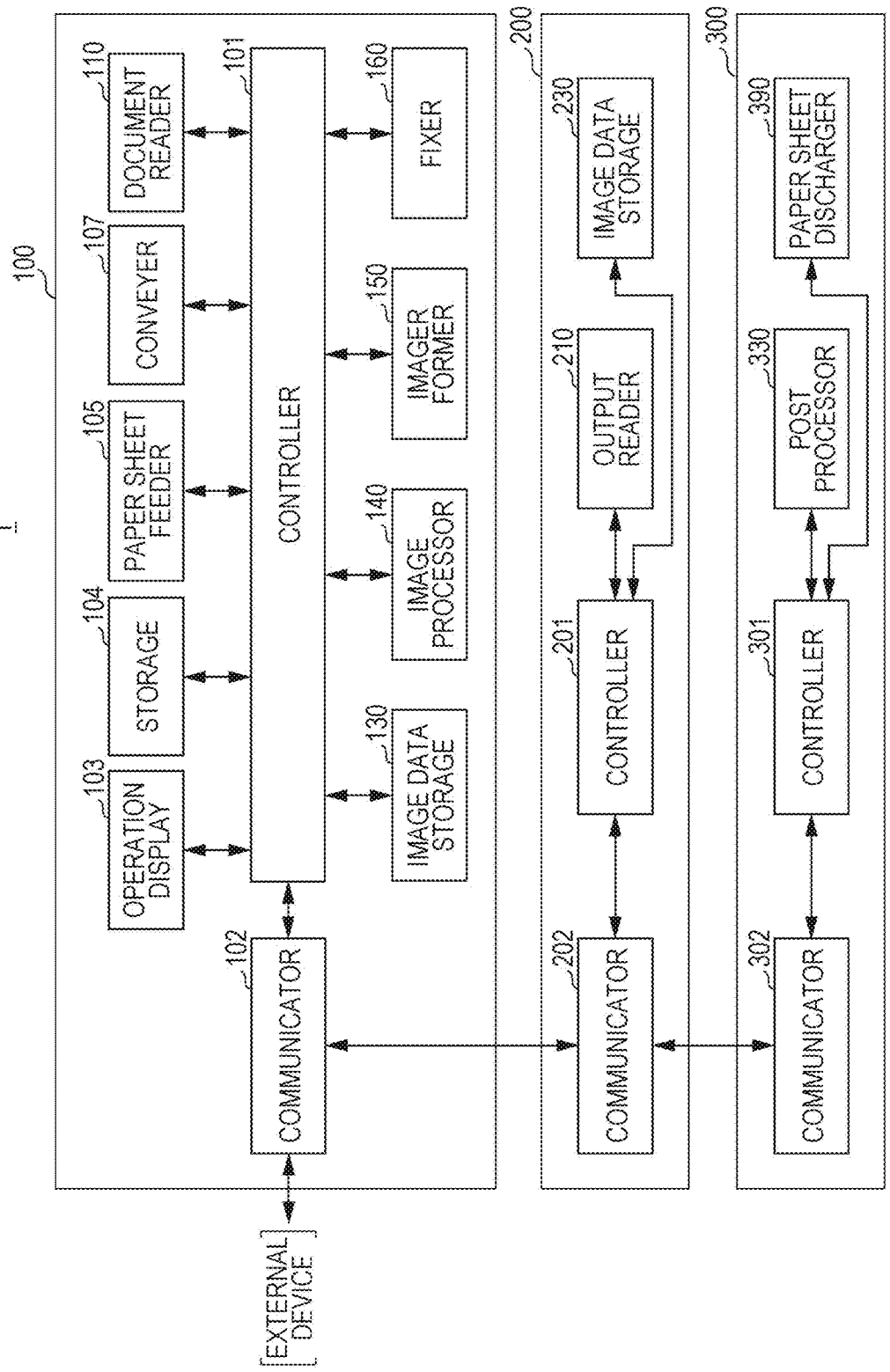
FIG. 1 is a configuration diagram illustrating a configuration according to an embodiment of the present invention.
Figure 2:
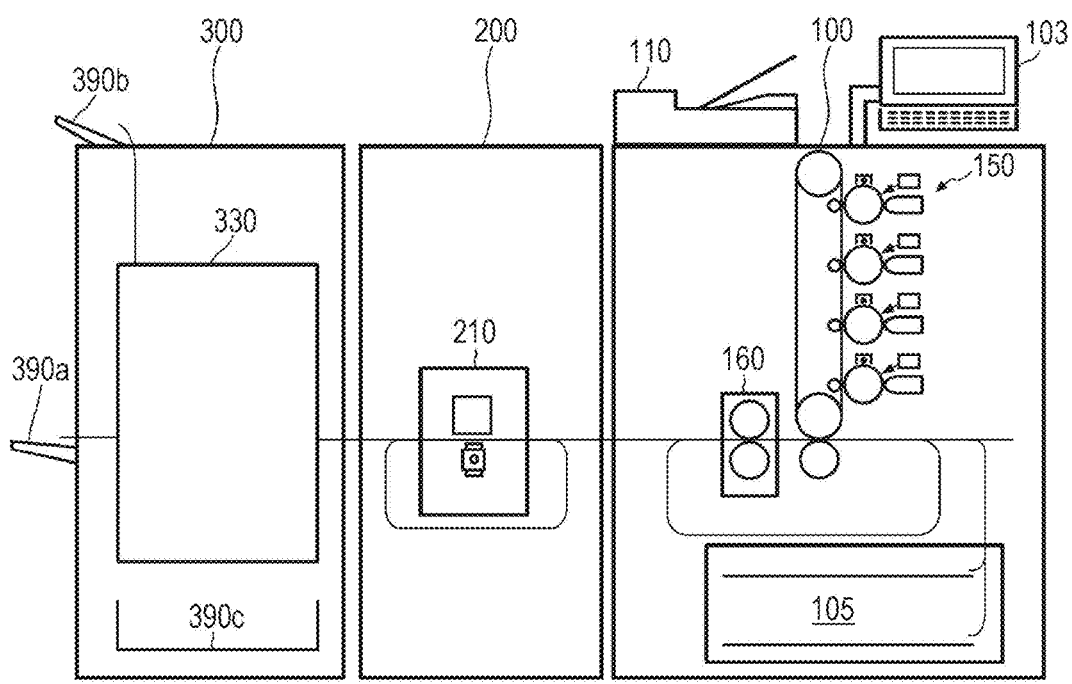
FIG. 2 is a configuration diagram illustrating a configuration according to an embodiment of the present invention.

A first configuration example of an image forming system 1 including a control device, a reading device, and an image forming device will be described in detail with reference to FIGS. 1 and 2. FIG. 1 is a functional block diagram illustrating functions of respective components included in the image forming system 1, and FIG. 2 is an explanatory diagram illustrating mechanical elements of respective components of the devices included in the image forming system 1.

In the image forming system 1 according to the present embodiment, an image forming device 100, a reading device 200, and a post processing device 300 are arranged to be connected to each other along a paper sheet conveying direction.

Here, the image forming device 100 includes a controller 101 that controls each component in the image forming device 100, a communicator 102 that communicates with other connected devices, an operation display 103 that receives an operation input by a user and displays a state of the image forming device 100, a storage 104 that stores various settings, a paper sheet feeder 105 that can feed a paper sheet stored in a paper feed tray, a conveyer 107 that conveys the paper sheet in the device, a document reader 110 that reads a document on a platen, an image data storage 130 that stores image data and various data when an image is formed, an image processor 140 that performs various image processing necessary for image formation, an imager former 150 that forms an image on the paper sheet based on an image forming command and the image data, and a fixer 160 that stabilizes the image formed on the paper sheet using toner with heat and pressure. As illustrated in FIG. 2, the imager former 150 is a so-called electrographic image former that forms toner images by developing electrostatic latent images formed on charged image carriers and overlaps the toner images of respective colors on an intermediate transfer body and transfers the overlapped toner images on the paper sheet. However, the specific configuration of the imager former 150 is not limited to that illustrated in FIG. 2.

The reading device 200 includes a controller 201 that controls each component in the reading device 200, a communicator 202 that communicates with other devices, an output reader 210 that reads the images on the paper sheet being conveyed, and an image data storage 230 that temporarily stores reference image data and read image data.

The post processing device 300 includes a controller 301 that controls each component in the post processing device 300, a communicator 302 that communicates with other devices, a post processor 330 that performs various post processing such as cutting, punching, and stapling on a sheet paper, and a paper sheet discharger 390 that discharges the paper sheet.

Here, a content of the processing by the post processor 330 is not particularly limited. However, various post processing including at least cutting, stapling, punching, and folding can be performed on each paper sheet or each bundle (booklet) including a plurality of paper sheets. When an image of an identification mark such as a register mark for distinguishing between an image forming area and an area to be cut is formed on a paper sheet at the time of image formation by the image forming device 100, the post processor 330 cuts the area to be cut with reference to the identification mark. Furthermore, the paper sheet discharger 390 includes paper sheet discharge trays 390a, 390b, and 390c, for example. Note that the configuration of the image forming system 1 illustrated in FIGS. 1 and 2 are merely examples, and more reading devices and more post processing devices may be coupled.

As illustrated in FIG. 3, it is possible that the image forming system 1 includes the image forming device 100 and the reading device 200, the paper sheet discharged on a paper sheet discharger 290 of the reading device 200 is transferred to a paper sheet feeder 305 of the post processing device 300 that is not connected to the image forming system 1, and post processing is performed by the post processing device 300. In this case, at the time of image formation by the image forming device 100, the image of the identification mark such as a register mark for distinguishing between the image forming area and the area to be cut is formed on the paper sheet. Then, the post processing device 300 cuts the area to be cut with reference to the identification mark.

In the first configuration example, the controller 201 in the reading device 200 forms a control device that determines whether an abnormality occurs in the image formed on the paper sheet with reference to image forming information regarding image formation in which the area to be cut is provided in the paper sheet and the image is formed in the image forming area and read image information generated according to the reading of the image formed on the paper sheet and generates control information for controlling image information by the image forming device and generates control information for adjusting positions of the image forming area and the area to be cut so as to move the abnormality to the area to be cut in a case where the abnormality is detected in the image forming area. An operation as the control device is realized by a control program.

[Configuration (2)]

Figure 4:
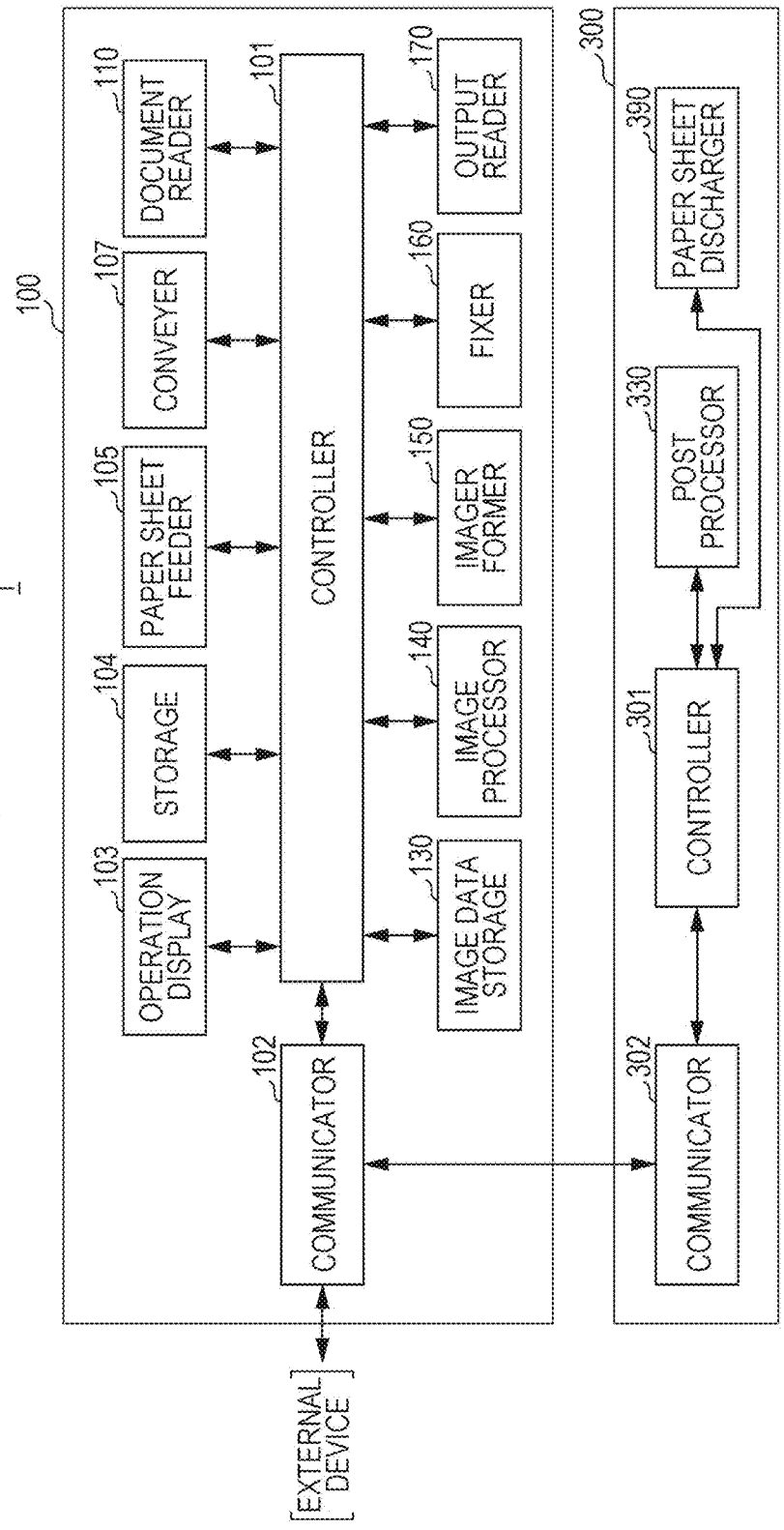
FIG. 4 is a configuration diagram illustrating a configuration according to an embodiment of the present invention.
Figure 5:
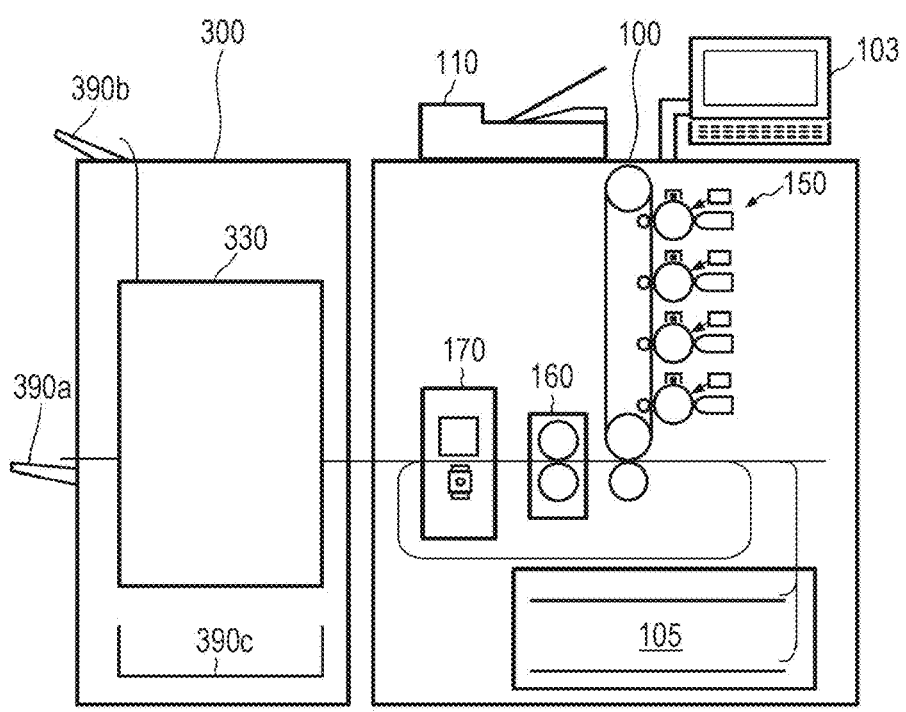
FIG. 5 is a configuration diagram illustrating a configuration according to an embodiment of the present invention.

A second configuration example of an image forming system 1 including a control device, a reading device, and an image forming device will be described in detail with reference to FIGS. 4 and 5. FIG. 4 is a functional block diagram illustrating functions of respective components included in the image forming system 1, and FIG. 5 is an explanatory diagram illustrating mechanical elements of respective components of the devices included in the image forming system 1. In the second configuration example of the image forming system 1, components same as those in the first configuration example illustrated in FIGS. 1 and 2 are denoted with the same reference numerals to omit overlapped description. In the image forming system 1, an output reader 170 as a reading device for reading an image formed on the paper sheet is provided in the image forming device 100. Therefore, in the image forming system 1, the reading device 200 is not connected. It is possible to provide an intermediate device instead of the reading device 200 and arrange an inverter and the like. Note that the output reader 170 reads the image formed on the paper sheet and arranged on the downstream side of the imager former 150 and the fixer 160 and reads the image while the paper sheet is conveyed. Note that the configuration of the image forming system 1 illustrated in FIGS. 4 and 5 are merely examples, and more reading devices and more post processing devices may be coupled.

In the second configuration example, the controller 101 forms a control device that determines whether an abnormality occurs in the image formed on the paper sheet with reference to image forming information regarding image formation in which the area to be cut is provided in the paper sheet and the image is formed in the image forming area and read image information generated according to the reading of the image formed on the paper sheet and generates control information for controlling image formation by the image forming device and generates control information for adjusting positions of the image forming area and the area to be cut so as to move the abnormality to the area to be cut in a case where the abnormality is detected in the image forming area. An operation as the control device is realized by a control program.

[Configuration (3)]

Figure 6:
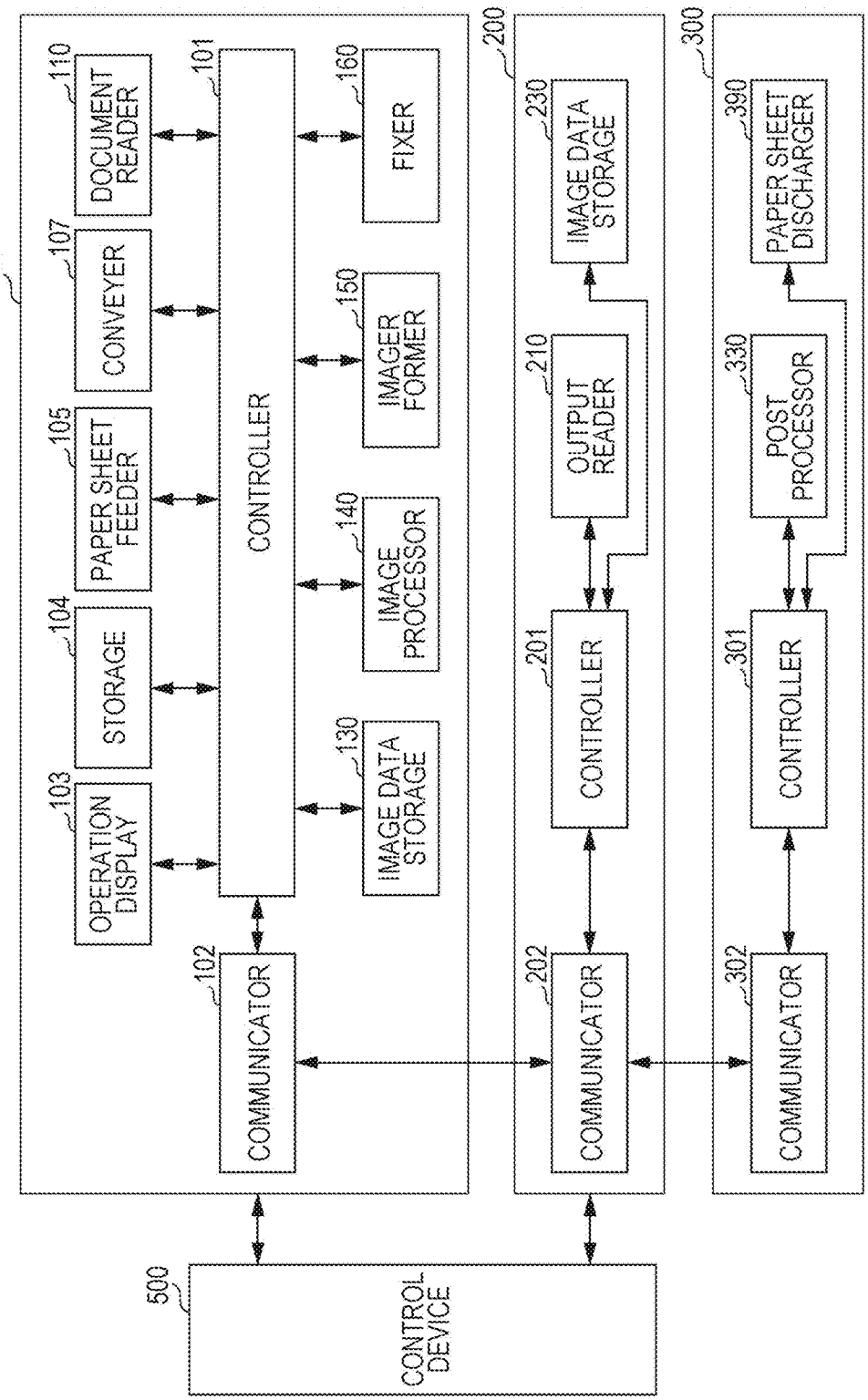
FIG. 6 is a configuration diagram illustrating a configuration according to an embodiment of the present invention.

A third configuration example of an image forming system 1 including a control device, a reading device, and an image forming device will be described in detail with reference to FIG. 6. FIG. 6 is a functional block diagram illustrating a function of each component in each device included in the image forming system 1. In the third configuration example of the image forming system 1, components same as those in the first configuration example illustrated in FIGS. 1 and 2 are denoted with the same reference numerals to omit overlapped description.

In the image forming system 1, a control device 500 that can communicate with the image forming device 100 and the reading device 200 is provided. Note that the control device 500 may be directly connected to the image forming device 100 and the reading device 200 and may be capable of communicating with the image forming device 100 and the reading device 200 via a network.

The control device 500 is a control device that determines whether an abnormality occurs in the image formed on the paper sheet with reference to image forming information regarding image formation in which the area to be cut is provided in the paper sheet and the image is formed in the image forming area and read image information generated according to the reading of the image formed on the paper sheet and generates control information for controlling image formation by the image forming device and generates control information for adjusting positions of the image forming area and the area to be cut so as to move the abnormality to the area to be cut in a case where the abnormality is detected in the image forming area. An operation as the control device is realized by a control program.

[Operation]

Hereinafter, an operation of a basic embodiment will be described with reference to a flowchart in FIG. 7. Here, an operation in the first configuration example of the image forming system 1 in FIGS. 1 and 2 will be described as a specific example. The following operation is realized by a control program in the controller.

The image forming device 100 receives an instruction regarding image formation from a user via the operation display 103 or receives the instruction from an external device via the communicator 102 (step S100 in FIG. 7). The instruction regarding image formation includes an instruction to start image formation, designation of image data of the image to be formed, designation of the area to be cut and the image forming area, designation of post processing, and the like.

When the image data of the image to be formed is designated, the controller 101 calls the image data to form the image regarding the designated image data from the image data storage 130, performs image processing necessary for image formation by the image processor 140, and transmits the image data on which the image processing is performed to the imager former 150.

Furthermore, in parallel to the processing for forming the image, the controller 101 transmits various information such as the image data on which the image processing is performed to form the image, the reference image data to be a comparison reference to detect the abnormality, and information regarding designation of the area to be cut and the image forming area to the reading device 200 as the image forming information regarding image formation (step S101 in FIG. 7). Since the reference image data is image data for forming the image of the imager former 150, the reference image data includes an image in an image area, an identification mark for dividing the image area and the area to be cut, and a blank image in the area to be cut, and the like.

The controller 201 of the reading device 200 receives the image forming information including various information such as the reference image data and the information regarding the designation of the area to be cut and the image forming area, and the like transmitted from the image forming device 100 and temporarily stores the information to the image data storage 230 (step S201 in FIG. 7).

Here, the controller 101 of the image forming device 100 controls the paper sheet feeder 105, the conveyer 107, the image data storage 130, the image processor 140, the imager former 150, and the fixer 160 so as to form an image instructed from the operation display 103 and an external connection device (step S102 in FIG. 7). That is, the controller 101 instructed to start to form the image controls each component so that the paper sheet is fed from the paper sheet feeder 105 to the imager former 150, the image processing is performed on the image data read from the image data storage 130 by the image processor 140, the image is formed on the paper sheet by the imager former 150, and the image on the paper sheet is stabilized by the fixer 160 with heat and pressure.

In this image formation, the area to be cut and the image forming area are set on the paper sheet, and the identification mark such as a register mark for distinguishing the image forming area and the area to be cut is formed on the paper sheet.

Then the controller 101 controls the conveyer 107 to convey the paper sheet, on which the image is formed, from the image forming device 100 toward the reading device 200 (step S103 in FIG. 7).

Under the control by the controller 201, the reading device 200 that receives the conveyed paper sheet from the image forming device 100 reads the entire paper sheet including the area to be cut and the image forming area by the output reader 210, generates read image data, and makes the image data storage 230 store the data (step S202 in FIG. 7).

Here, the controller 201 reads the reference image data and the read image data in the image forming information transmitted from the image forming device 100 from the image data storage 230 and compares and checks the data (step S203 in FIG. 7). Specifically, the identification mark, the image in the identification mark (image area), and a blank outside the identification mark (area to be cut) in the read image data are respectively compared with the identification mark, the image in the identification mark (image area), and a blank outside the identification mark (area to be cut) included in the reference image data to confirm whether inconsistency (abnormality) caused by a contamination or a missing pail of an image occurs.

In a case where the read image data and the reference image data coincide with each other and an abnormality is not recognized (NO in step S204 in FIG. 7), the controller 201 notifies the controller 101 of the image forming device 100 of normality (step S209 in FIG. 7).

The controller 101 that receives the notification indicating normality from the controller 201 ("normal" in steps S104 and S105 in FIG. 7) repeatedly forms designated images to the final page (steps S110 to S101 and S110 to the end in FIG. 7).

In addition, inconsistency (abnormality) in any portion in comparison between the image forming area in the read image data and the reference image data is recognized (YES in step S204 in FIG. 7), the controller 201 confirms whether cutting is designated with reference to the image forming information or whether the identification mark exists with reference to the read image data, that is, cutting is planned in the post processing (step S205 in FIG. 7).

If the plan to cut cannot be confirmed (NO) in step S205 in FIG. 7), the abnormality in the image area cannot be moved and escaped to the area to be cut. Therefore, the controller 201 notifies the controller 101 of the image forming device 100 of an error caused by the abnormality in the image area (step S211 in FIG. 7).

The controller 101 that receives the notification of the error caused by the abnormality from the controller 201 ("abnormality" in steps S104 and S105 in FIG. 7) performs control to stop the paper sheet feeder 105, the conveyer 107, the image data storage 130, the image processor 140, the imager former 150, and the fixer 160 so as to stop image formation (step S108 in FIG. 7). In addition, the controller 101 displays that the image formation is stopped due to the abnormality on the operation display 103 and informs the external device of the stop via the communicator 102 as necessary (step S109 in FIG. 7).

On the other hand, in a case where some abnormality is recognized in the comparison between the read image data and the reference image data (YES in step S204 in FIG. 7) and in a case where it can be confirmed that cutting is planned in the post processing with reference to the image forming information and the read image data (YES in step S205 in FIG. 7), the controller 201 confirms whether the position where the abnormality is detected is in the area to be cut or the image area (step S206 in FIG. 7).

In a case where the post processing such as punching or stapling is planned in the image area, a post processing position on which the post processing is performed and an intermediate area between the area to be cut and the post processing position are included in the area to be cut.

When the detected abnormality exists in the area to be cut (YES in step S206 in FIG. 7), an abnormality does not appear on the final printed matter that has been cut. Therefore, the detected abnormality is recognized as the normality described above, and the normality is notified to the controller 101 of the image forming device 100 (step S209 in FIG. 7). As described above, since the abnormality does not appear in a state of the printed matter in a case where the abnormality exists in the post processing position and the intermediated area between the area to be cut and the post processing position, the normality is notified to the controller 101 of the image forming device 100 (step S209 in FIG. 7). The controller 101 that receives the notification indicating normality from the controller 201 ("normal" in steps S104 and S105 in FIG. 7) repeatedly forms designated images to the final page (steps S110 to S101 and S110 to the end in FIG. 7).

If the detected abnormality exists in the image area, not in the area to be cut (NO in step S206 in FIG. 7), the controller 201 performs calculation to adjust the positions of the image forming area and the area to be cut so that the abnormality in the image forming area is moved and escaped to the area to be cut (step S207 in FIG. 7).

When it is determined that the abnormality in the image forming area cannot be moved and escaped to the area to be cut even if the positions of the image forming area and the area to be cut are adjusted as a result of the calculation (NO in step S208 in FIG. 7), the controller 201 notifies the controller 101 of the image forming device 100 of the error caused by the abnormality in the image area (step S211 in FIG. 7). The controller 101 that has received the notification of the error caused by the abnormality from the controller 201 ("abnormality" in steps S104 and S105 in FIG. 7) performs control to stop image formation (step S108 in FIG. 7), displays that the image formation is stopped due to the abnormality on the operation display 103, and informs the external device that the image formation is stopped via the communicator 102 as necessary (step S109 in FIG. 7).

On the other hand, when it is determined that the abnormality in the image forming area can be moved and escaped to the area to be cut by adjusting the positions of the image forming area and the area to be cut as a result of the calculation (YES in step S208 in FIG. 7), the controller 201 generates control information to adjust the positions of the image forming area and the area to be cut so that the abnormality is moved to the area to be cut and notifies the controller 101 of the image forming device 100 of the control information (step S210 in FIG. 7). For example, methods for adjusting the positions include moving the image forming area in at least one of a main scanning direction and a sub scanning direction in the paper sheet, rotating the image forming area in the paper sheet, moving the position of the paper sheet in the main scanning direction at the time when the image is formed by the image forming device, moving a timing when the image is formed by the image forming device on the paper sheet in the sub scanning direction, and the like.

The controller 101 that has received the control information from the controller 201 ("control information" in steps S104 and S105 in FIG. 7) adjusts the position of the image forming area and the area to be cut indicated in the control information by the image processor 140 with respect to image data same as that in which the abnormality has been detected (step S106 in FIG. 7) and controls each component to form an image by using the image data in which the positions have been adjusted (step S107 in FIG. 7).

Furthermore, the image may be formed by performing adjustment according to the control information form next image data instead of the image data same as that in which the abnormality has been detected.

After that, until next new control information is notified, the controller 101 maintains the state where the positions have been adjusted and repeatedly forms designated images to the final page while controlling the image processor 140 so that the position where the abnormality appears is located in the area to be cut (step S110 to S101 and S110 to end in FIG. 7). As described later, the state to be maintained includes various states such as movement of the position, rotation of the position, a paper sheet conveyance timing and a position of the paper sheet in the main scanning direction.

The controller 201 that has notified the normality (step S209 in FIG. 7), notified the control information (step S210 in FIG. 7), and notifies the abnormality (step S211 in FIG. 7) repeatedly performs processing on new paper sheets from the image forming device 100 to the final page (step S212 to S201 and S212 to end in FIG. 7).

[Specific Example of Position Adjustment]

Hereinafter, the position adjustment of the image forming area and the area to be cut to move and escape the abnormality in the image forming area to the area to be cut will be described with reference to the drawings and using a specific example.

Figure 8A:
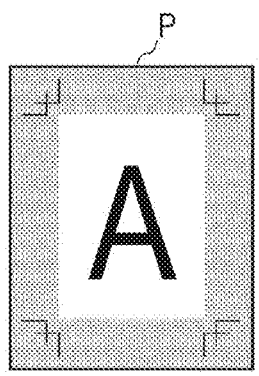
FIGS. 8A to 8C are explanatory diagrams of exemplary processing according to an embodiment of the present invention.
Figure 8B:
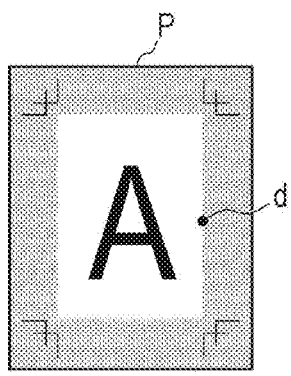
Figure 8C:
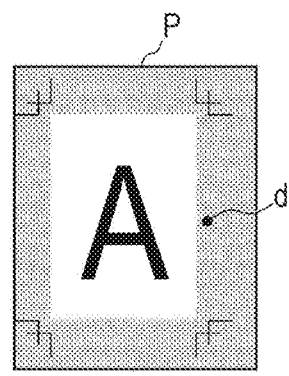

In FIG. 8A, the reference image data or normal read image data is exemplified in which four identification marks formed by combining letters L are arranged and the image forming area (white portion) and the area to be cut (gray portion) can be distinguished from each other on a paper sheet P. Here, FIG. 8B illustrates a state where a contamination d that causes an abnormality is detected in the image forming area (white portion) on the paper sheet P in the read image data. In a case where the contamination d exists as in FIG. 8B, the position of the contamination d can be escaped to the area to be cut (gray portion) by moving the image area to the direction opposite to the position of the contamination d in the paper sheet P as in FIG. 8C.

Figure 9A:
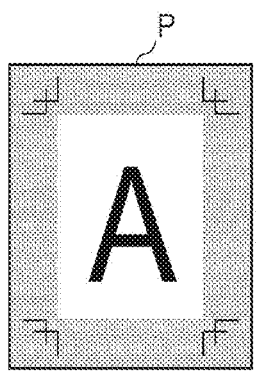
FIGS. 9A to 9E are explanatory diagrams of exemplary processing according to an embodiment of the present invention.
Figure 9B:
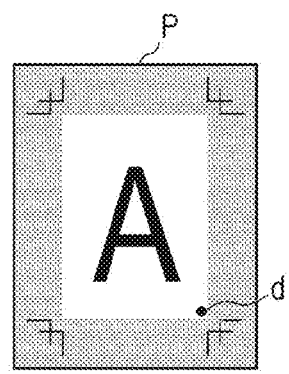
Figure 9C:
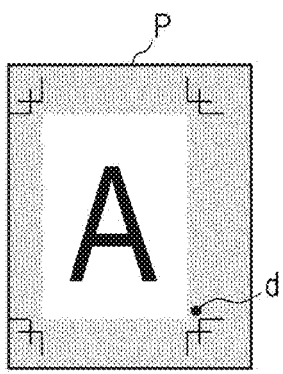
Figure 9D:
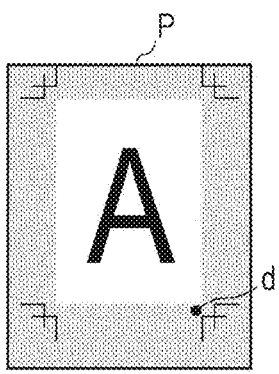
Figure 9E:
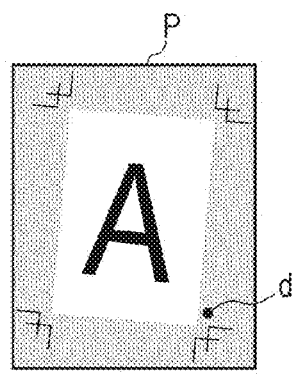

In FIG. 9A, the reference image data or normal read image data is exemplified in which four identification marks formed by combining letters L are arranged and the image forming area (white portion) and the area to be cut (gray portion) can be distinguished from each other on the paper sheet P. Here, FIG. 9B illustrates a state where the contamination d that causes an abnormality is detected in the image forming area (white portion) on the paper sheet P in the read image data. In a case where the contamination d as in FIG. 9B exists in the vicinity of a lower right portion in FIG. 9B, the position of the contamination d can be escaped to the area to be cut (gray portion) by moving the image area to the left side in the paper sheet P as in FIG. 9C. In a case where the contamination d as in FIG. 9B exists in the vicinity of a lower right portion in FIG. 9B, the position of the contamination d can be escaped to the area to be cut (gray portion) by moving the image area to the upper side in the paper sheet P as in FIG. 9D. In addition, in a case where the contamination d exists in the vicinity of the lower right portion as in FIG. 9B, the contamination d in the lower right portion can be escaped to the area to be cut (gray portion) by rotating the image area in the paper sheet P as in FIG. 9E. Incidentally, in consideration of a load of the image processing, it is desirable that horizontal movement in FIGS. 9C and 9D is a first candidate and rotational movement in FIG. 9E is a second candidate.

Figure 10A:
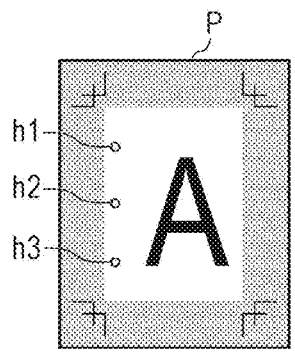
FIGS. 10A to 10C are explanatory diagrams of exemplary processing according to an embodiment of the present invention.
Figure 10B:
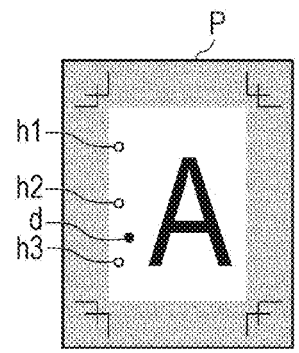
Figure 10C:
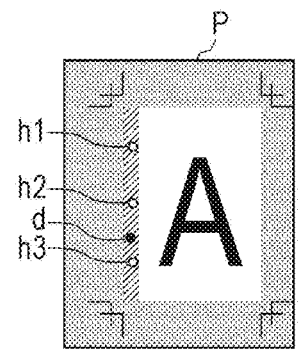

In FIG. 10A, the reference image data or normal read image data is exemplified in which four identification marks formed by combining letters L are arranged and the image forming area (white portion) and the area to be cut (gray portion) can be distinguished from each other on the paper sheet P. Here, as the post processing, making punching holes h1 to h3 is planned in addition to culling. Here, FIG. 10B illustrates a state where a contamination d that causes an abnormality is detected in the image forming area (white portion) on the paper sheet P and in the vicinity of the punching holes h1 to h3 in the read image data. In a case where the contamination d exists in the vicinity of the punching holes h1 to h3 as in FIG. 10B, it is possible to position the contamination d in an area between an extension line of the punching holes h1 to h3 and the area to be cut closest to the extension line (hatched portion in FIGS. 10A to 10C: area near post processing) by moving the image area to the direction opposite to the position of the contamination d in the paper sheet P as in FIG. 10C. That is, the area near post processing is used similarly to the area to be cut, and the contamination d is moved. Since the image is not formed in the area near post processing, a printed matter does not become defective.

Figure 11A:
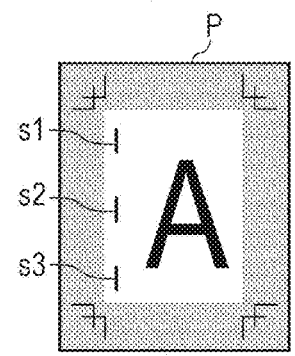
FIGS. 11A to 11C are explanatory diagrams of exemplary processing according to an embodiment of the present invention.
Figure 11B:
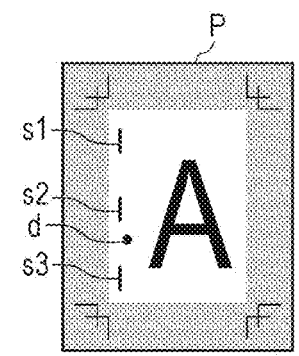
Figure 11C:
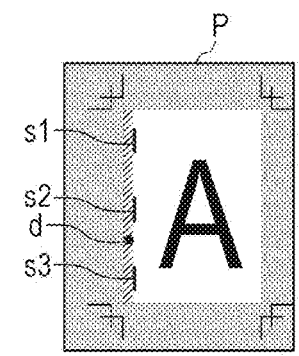

In FIG. 11A, the reference image data or normal read image data is exemplified in which four identification marks formed by combining letters L, are arranged and the image forming area (white portion) and the area to be cut (gray portion) can be distinguished from each other on the paper sheet P. Here, as the post processing, making staples s1 to s3 are planned in addition to cutting. Here, FIG. 11B illustrates a state where the contamination d that causes an abnormality is detected in the image forming area (white portion) on the paper sheet P and in the vicinity of the staples s1 to s3 in the read image data. In a case where the contamination d exists in the vicinity of the staples s1 to s3 as in FIG. 11B, it is possible to position the contamination d in an area between an extension line of the staples s1 to s3 and the area to be cut closest to the extension line (hatched portion in FIGS. 11A to 11C: area near post processing) by moving the image area to the direction opposite to the position of the contamination d in the paper sheet P as in FIG. 11C. That is, the area near post processing is used similarly to the area to be cut, and the contamination d is moved.

Figure 12A:
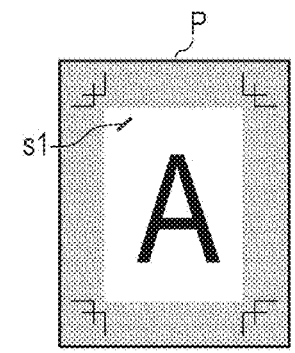
FIGS. 12A to 12C are explanatory diagrams of exemplary processing according to an embodiment of the present invention.
Figure 12B:
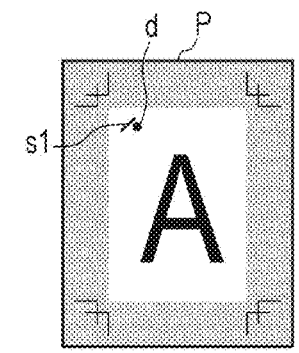
Figure 12C:
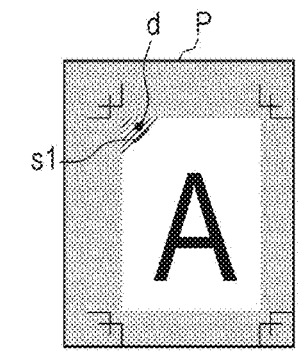

In FIG. 12A, the reference image data or normal read image data is exemplified in which four identification marks formed by combining letters L, are arranged and the image forming area (white portion) and the area to be cut (gray portion) can be distinguished from each other on the paper sheet P. Here, as the post processing, making a staple s1 is planned in addition to cutting. Here, FIG. 12B illustrates a state where the contamination d that causes an abnormality is detected in the image forming area (white portion) on the paper sheet P and in the vicinity of the staple s in the read image data. In a case where the contamination d exists in the vicinity of the staple s1 as in FIG. 12B, it is possible to position the contamination d in an area between an extension line of the staple s1 to and the area to be cut closest to the extension line (hatched portion in FIGS. 12A to 12C: area near post processing) by moving the image area to the direction opposite to the position of the contamination d in the paper sheet P as in FIG. 12C. That is, the area near post processing is used similarly to the area to be cut, and the contamination d is moved.

Figure 13A:
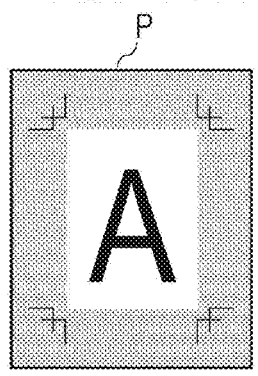
FIGS. 13A to 13C are explanatory diagrams of exemplary processing according to an embodiment of the present invention.
Figure 13B:
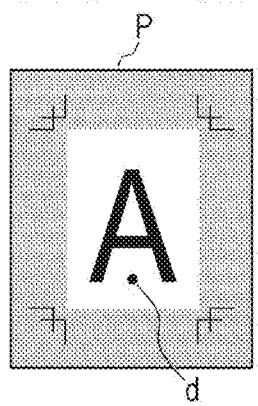
Figure 13C:
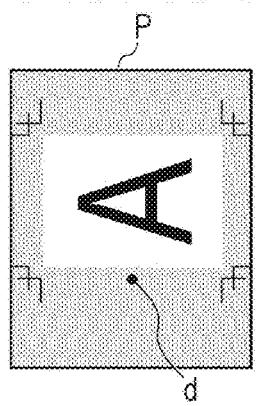

In FIG. 13A, the reference image data or normal read image data is exemplified in which four identification marks formed by combining letters L, are arranged and the image forming area (white portion) and the area to be cut (gray portion) can be distinguished from each other on the paper sheet P. Here, FIG. 13B illustrates a state where the contamination d that causes an abnormality is detected in the image forming area (white portion) on the paper sheet P in the read image data. In a case of FIG. 13B, due to the position of the contamination d, the contamination d cannot be escaped by the horizontal movement or the vertical movement of the image area. Therefore, as illustrated in FIG. 13C, by rotating the image area by 90° in the paper sheet P and moving the image area upward in FIG. 13C, a large area to be cut (gray portion) can be secured on the lower side of FIG. 13C in the paper sheet P, and the contamination d can be escaped to the area to be cut. In consideration of the load of image processing, it is desirable that the horizontal movement and the vertical movement described above be a first candidate and rotational movement in FIG. 13C be a second candidate.

Figure 14A:
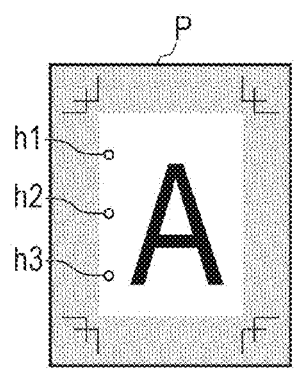
FIGS. 14A to 14C are explanatory diagrams of exemplary processing according to an embodiment of the present invention.
Figure 14B:
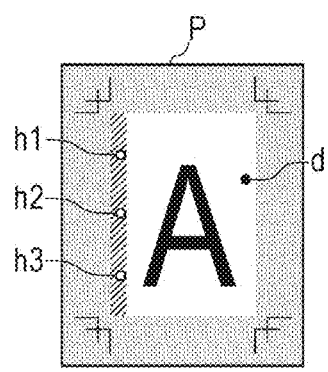
Figure 14C:
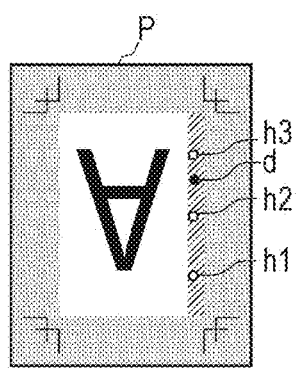

In FIG. 14A, the reference image data or normal read image data is exemplified in which four identification marks formed by combining letters L are arranged and the image forming area (white portion) and the area to be cut (gray portion) can be distinguished from each other on the paper sheet P. Here, as the post processing, making punching holes h1 to h3 is planned in addition to cutting. Here, FIG. 14B illustrates a state where the contamination d that causes an abnormality is detected in the image forming area (white portion) on the paper sheet P and on the opposite side of the punching holes h1 to h3 in the read image data. In a case where the contamination d exists in the vicinity of the punching holes h1 to h3 as in FIG. 14B and in a case where the positions of the punching holes h1 to h3 can be changed, the image area is rotated in the paper sheet P as in FIG. 14C so as to position the area near post processing (hatched portion) at the position of the contamination d. That is, the area near post processing is used similarly to the area to be cut, and the contamination d is moved by rotating the image area by 180°. Since the image is not formed in the area near post processing, a printed matter does not become defective.

Figure 15A:
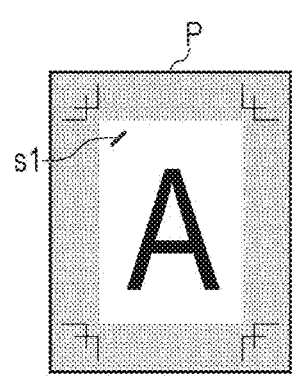
FIGS. 15A to 15C are explanatory diagrams of exemplary processing according to an embodiment of the present invention.
Figure 15B:
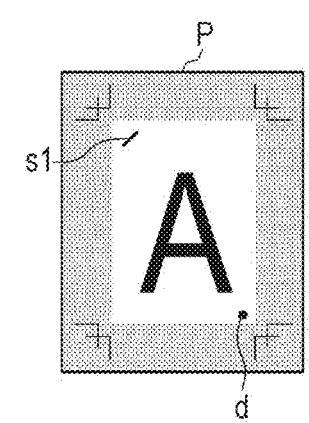
Figure 15C:
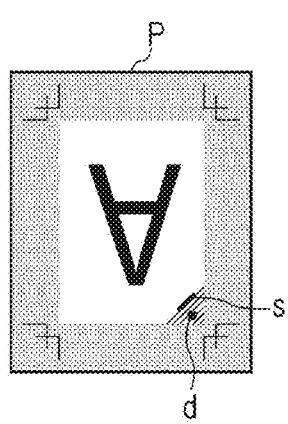

In FIG. 15A, the reference image data or normal read image data is exemplified in which four identification marks formed by combining letters L are arranged and the image forming area (white portion) and the area to be cut (gray portion) can be distinguished from each other on the paper sheet P. Here, as the post processing, making a staple s1 is planned in addition to cutting. Here, FIG. 15B illustrates a state where the contamination d that causes an abnormality is detected in the image forming area (white portion) on the paper sheet P and on the side 180° opposite to the staple s1 in the read image data. In a case where the contamination d exists in the vicinity of the staple s1 as in FIG. 15B and in a case where the position of the staple s1 can be changed, the image area is rotated in the paper sheet P as in FIG. 5C so as to position the area near post processing (hatched portion) at the position of the contamination d. That is the area near post processing is used similarly to the area to be cut, and the contamination c is moved by rotating the image area by 180°. Since the image is not formed in the area near post processing, a printed matter does not become defective.

Figure 16A:
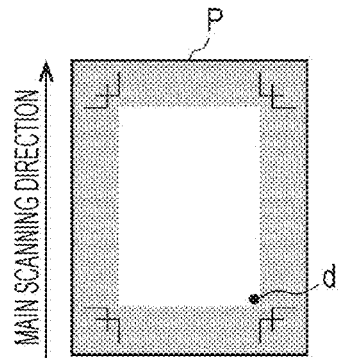
FIGS. 16A to 16C are explanatory diagrams of exemplary processing according to an embodiment of the present invention.
Figure 16B:
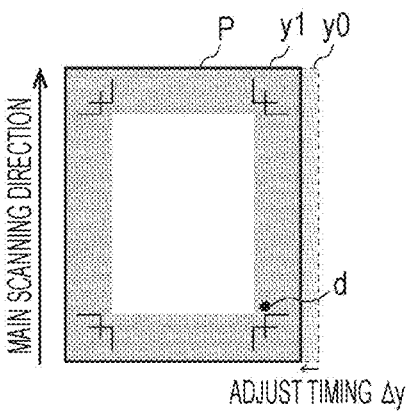

FIG. 16A illustrates a state where the contamination d that causes an abnormality is detected in the image forming area (white portion) on the paper sheet P in the read image data in which four identification marks formed by combining two letters L are arranged and the image forming area (white portion) and the area to be cut (gray portion) can be distinguished from each other in the paper sheet P.

Figure 16C:
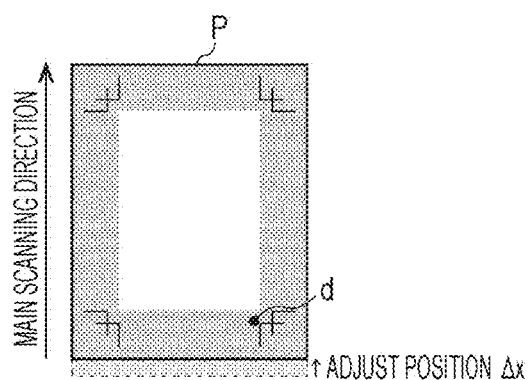

Here, the contamination d exists at the rear end in the paper sheet conveying direction (sub scanning direction) at the time when the image is formed. Therefore, as illustrated in FIG. 16C, by accelerating a conveyance timing (phase) of the paper sheet at the time when the image is formed, adjustment is made to position the contamination d in the area to be cut at the rear end in the paper sheet P. The contamination d can be escaped to the area to be cut (gray portion) with this method.

Furthermore, here, the contamination d exists at the left end in the main scanning direction at the time when the image is formed. Therefore, as illustrated in FIG. 16C, by shifting the position of the paper sheet in the main scanning direction to the right side at the time of image formation, adjustment is made to position the contamination d in the area to be cut at the left end in the paper sheet P. The contamination d can be escaped to the area to be cut (gray portion) with this method. Here, in a case where the paper sheet is moved in the main scanning direction in this way, it is necessary to move the paper sheet and image data for forming an image (exposure position on photosensitive member) by the same amount. The movement of the paper sheet in the main scanning direction can be realized by arranging a steering roller for adjusting the position and the direction of the paper sheet immediately before a resist roller for adjusting image transfer to the paper sheet.

[Specific Example of Abnormality Notification]

Hereinafter, a specific example of notification in a case where an abnormality occurs in the image will be described.

In a case where the abnormality occurs in the image and it is not possible to cope with the abnormality by moving the image area, it is preferable that an error be displayed similarly to a normal case.

Figure 17:
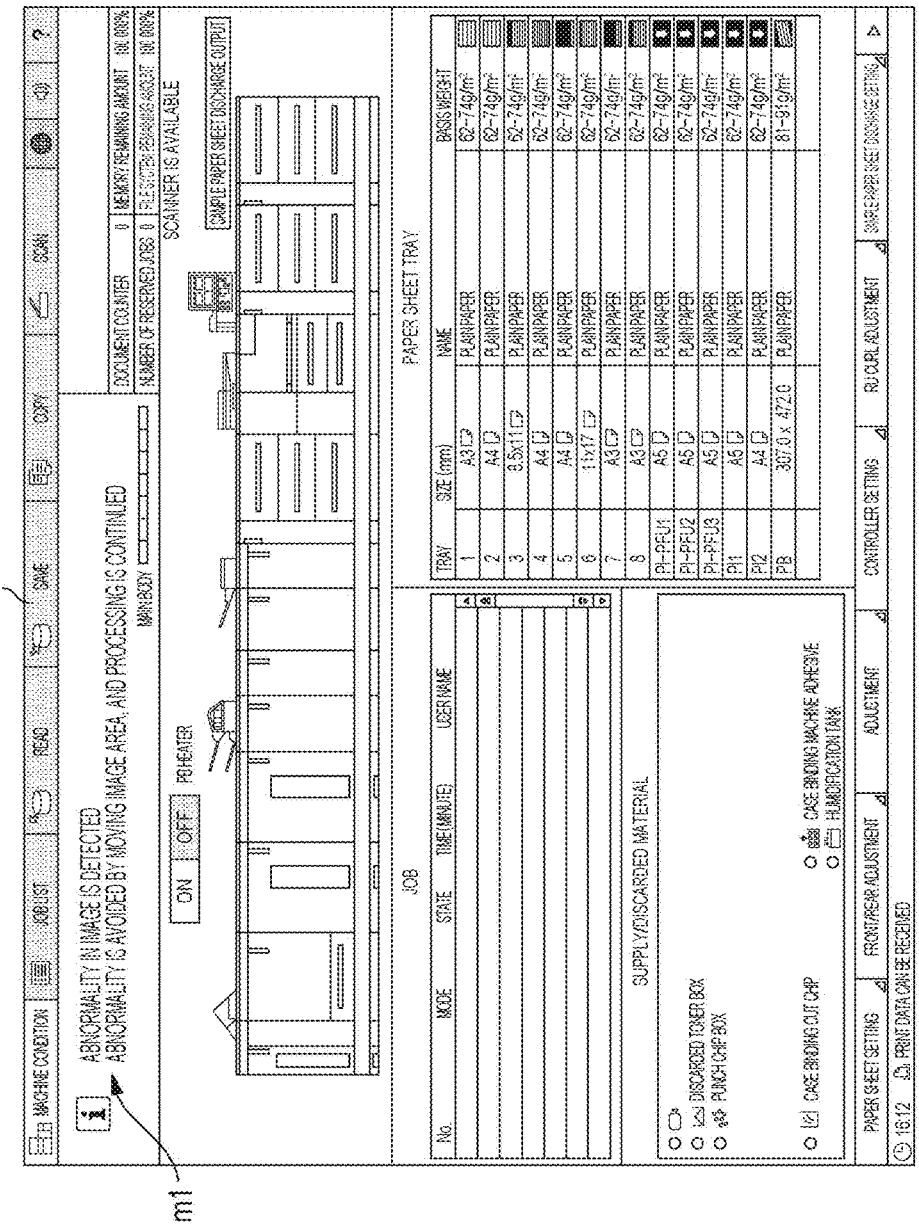
FIG. 17 is an explanatory diagram of exemplary notification according to an embodiment of the present invention.

In a case where the abnormality occurs in the image and the abnormality can be escaped to the area to be cut by moving the image area, the success of the escape can be displayed on the operation display 103 as in a message m1 in a display screen 103G1a in FIG. 17 by an instruction of the controller 101 that has received the notification from the controller 201.

Figure 18:
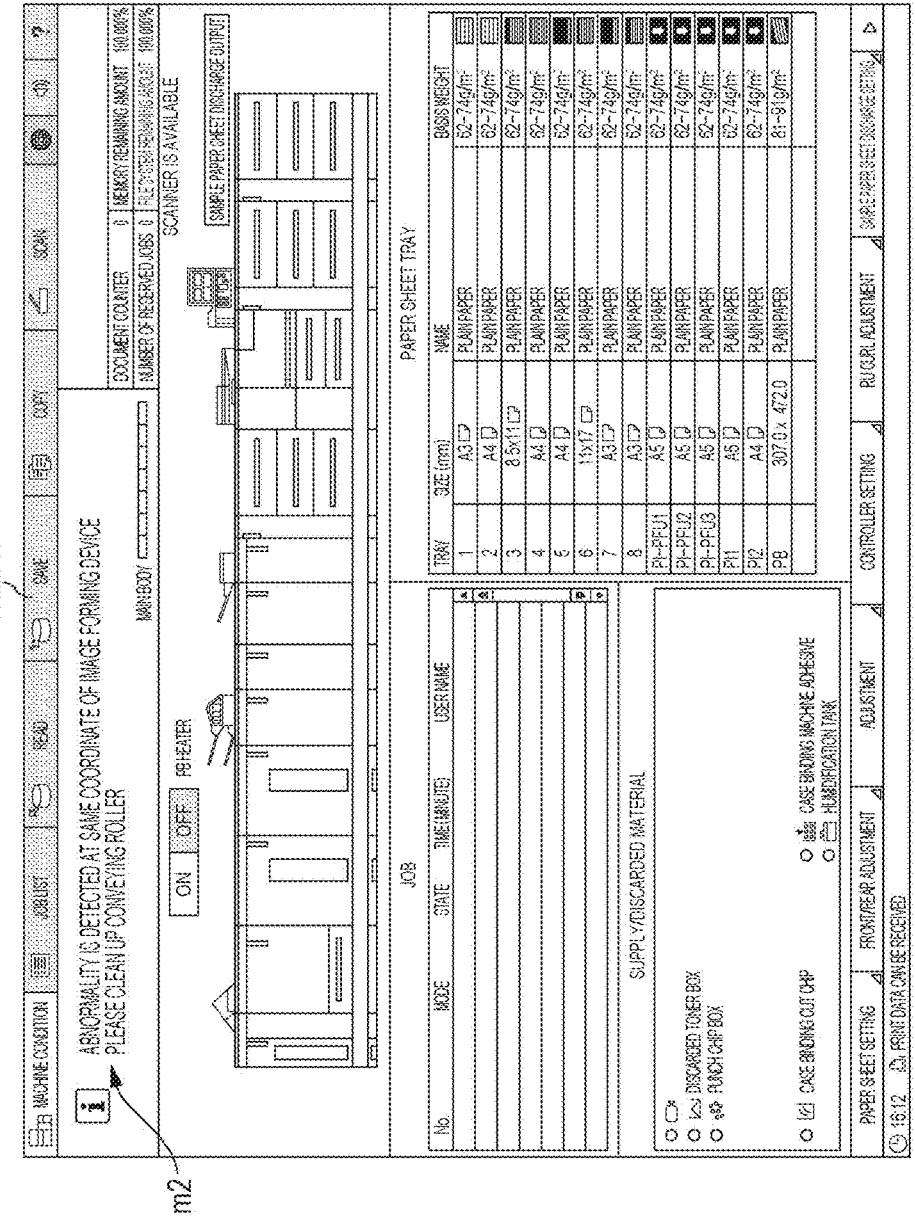
FIG. 18 is an explanatory diagram of exemplary notification according to an embodiment of the present invention.

Furthermore, in a case where the abnormalities are detected at the same coordinates in the image forming device 100 before and after the adjustment of the positions of the image area and the paper sheet, it is possible to display that the abnormality is caused by a mechanical factor in the image forming device 100 on the operation display 103 as in a message m2 in a display screen 103G1b in FIG. 18 by an instruction of the controller 101 that has received the notification from the controller 201. In this case, it is easy to take measures against the abnormality by this notification.

In addition, in a case where the abnormalities are detected at the same coordinates of reading positions of the reading device 200 before and after the adjustment of the positions of the image area and the paper sheet, it is possible to display that it is assumed that the abnormality is caused by a reading failure of a sensor of the output reader 210 in the reading device 200 on the operation display 103 by an instruction of the controller 101 that has received the notification from the controller 201. In this case, it is easy to take measures against the abnormality by this notification.

Similarly, in a case where the abnormalities are detected at the same coordinates in the image area before and after the adjustment of the positions of the image area and the paper sheet, it is possible to display that it is assumed that the abnormality is caused by a factor in the image processing of the image processor 140 or an image forming process of the imager former 150 on the operation display 103 by an instruction of the controller 101 that has received the notification from the controller 201. In this case, it is easy to take measures against the abnormality by this notification.

In addition to the display on the operation display 103, the notification of the cause of the abnormality as described above can be notified to the external device via the communicator 102.

[Other Embodiments]

In the above description, it has been assumed that the control device that is a characteristic part of the present embodiment exist in the reading device 200. However, as illustrated in FIG. 6, it is possible that the control device 500 that can communicate with the image forming device 100 and the reading device 200 determines whether the abnormality occurs in the image and generates the control information to move the abnormality to the area to be cut. In this case, the control device 500 can remotely execute the control via the network.

Furthermore, as illustrated in FIGS. 4 and 5, the controller 101 in the image forming device 100 may perform all the characteristic control described above.

Further, in the above embodiment, for easy description, a state where the number of abnormalities (contamination d) is one is illustrated. In practice, since occurrence of a plurality of contaminations is expected, it is desirable to adjust the position of the image area and the paper sheet conveyance timing so as to move the plurality of contaminations to the area to be cut as possible.

Furthermore, by not only individually using but also combining the adjustment of the position of the image area, the adjustment of the paper sheet conveyance timing, and the adjustment of the position of the paper sheet in the main scanning direction, it is possible to effectively move the contaminations to the area to be cut.

According to an embodiment of the present invention, in a control device, a reading device, an image forming device, an image forming system, and a control program reflecting an aspect of an aspect of the present invention, the following effects can be obtained.

(1) The control device reflecting an aspect of the present invention determines whether an abnormality occurs in an image formed on a paper sheet with reference to image forming information and read image information, and generates control information to adjust positions of an image forming area and an area to be cut so as to move the abnormality to the area to be cut in a case where the abnormality has been detected in the image forming area and notifies an image forming device of the control information. Accordingly, the image forming device that has received the notification moves the abnormality to the area to be cut by adjusting the positions of the image forming area and the area to be cut according to the notification. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation.

(2) In (1), in a case where post processing such as punching or stapling is performed on the paper sheet on which the image has been formed, a post processing position and an intermediate area between the area to be cut and the post processing position, that is, an area near post processing is used similarly to the area to be cut. Accordingly, the image forming device that has received the notification moves the abnormality to the area to be cut including the area near post processing by adjusting positions of the image forming area except for the area near post processing and the area to be cut including the area near post processing according to the notification. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation. Furthermore, by including the area near post processing in the area to be cut, the abnormality is easily moved without deteriorating quality of the paper sheet.

(3) In (1) and (2), if the positions of the image forming area and the area to be cut can be adjusted, the image forming device that has received the notification forms the same image again after the adjustment based on the control information. As a result, the abnormality in the area to be cut is cut in the post processing and is not included in a printed matter, and it is possible to avoid finally making a defective printed matter and prevent downtime in image formation.

(4) In (1) to (3), since an image of an identification mark such as a register mark for distinguishing the image forming area and the area to be cut at the time when the image is formed is formed on the paper sheet, the image forming area and the area to be cut can be surely determined with reference to the identification mark included in the read image information.

(5) In (1) to (4), the control information to perform adjustment to move the abnormality to the area to be cut by moving the image forming area in at least one of a main scanning direction and a sub scanning direction in the paper sheet is generated and notified to the image forming device. Accordingly, the image forming device that has received the notification performs the adjustment to move the abnormality to the area to be cut by moving the image forming area in at leas one of the main scanning direction and the sub scanning direction in the paper sheet. As a result, since the abnormality in the area to be cut is not included in the printed matter by being cut off in post processing, it is possible to avoid finally making a defective printed matter and prevent downtime in image formation.

(6) In (1) to (5), control information to perform adjustment to move the abnormality to the area to be cut by moving the position of the paper sheet at the time of image formation by the image forming device in the main scanning direction is generated and notified to the image forming device. Accordingly, the image forming device that has received the notification performs the adjustment to move the abnormality to the area to be cut by moving the position of the paper sheet at the time of image formation in the main scanning direction. As a result, since the abnormality in the area to be cut is not included in the printed matter by being cut off in post processing, it is possible to avoid finally making a defective printed matter and prevent downtime in image formation.

(7) In (1) to (6), control information to perform adjustment to move the abnormality to the area to be cut by moving a timing when the image is formed on the paper sheet by the image forming device in the sub scanning direction is generated and notified to the image forming device. Accordingly, the image forming device that has received the notification performs the adjustment to move the abnormality to the area to be cut by moving the timing when the image is formed on the paper sheet by the image forming device in the sub scanning direction. As a result, since the abnormality in the area to be cut is not included in the printed matter by being cut off in post processing, it is possible to avoid finally making a defective printed matter and prevent downtime in image formation.

(8) In (1) to (7), in a case where the abnormalities are detected at the same coordinates in the image forming device before and after the adjustment of the positions of the image area and the paper sheet, it is informed that the abnormality is caused by a mechanical factor in the image forming device. As a result, it is easy to take measures against the abnormality. This makes it possible to prevent downtime in the image formation.

(9) In (1) to (8), in a case where abnormalities are detected at the same coordinates in the reading device before and after the adjustment of the positions of the image area and the paper sheet, it is informed that the abnormality is caused by a reading failure of the reading device. As a result, it is easy to take measures against the abnormality. This makes it possible to prevent downtime in the image formation.

(10) In (1) to (9), in a case where the abnormalities are detected at the same coordinates in the image area before and after the adjustment of the positions of the image area and the paper sheet, it is informed that the abnormality is caused by a factor in image processing or an image forming process. As a result, it is easy to take measures against the abnormality. This makes it possible to prevent downtime in the image formation.

(11) A reading device reflecting an aspect of the present invention includes the control device according to (1) to (10) and, in a case where an abnormality is detected in an image forming area, the reading device generates control information to adjust positions of an image forming area and an area to be cut to move the abnormality to the area to be cut and notifies an image forming device of the control information. Accordingly, the image forming device that has received the notification moves the abnormality to the area to be cut by adjusting the positions of the image forming area and the area to be cut according to the notification. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation.

(12) An image forming device reflecting an aspect of the present invention includes the control device according to (1) to (10) and, in a case where an abnormality is detected in an image forming area, the image forming device moves the abnormality to an area to be cut by adjusting positions of the image forming area and the area to be cut so as to move the abnormality to the area to be cut. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation.

(13) In (12), in a case where the abnormality is detected in the image forming area and the positions of the image forming area and the area to be cut can be adjusted, the same image is formed again after the adjustment based on the control information. As a result, the abnormality in the area to be cut is cut in the post processing and is not included in a printed matter, and it is possible to avoid finally making a defective printed matter and prevent downtime in image formation.

(14) In (12) and (13), since an image of an identification mark such as a register mark for distinguishing the image forming area and the area to be cut at the time when the image is formed is formed on the paper sheet, the image forming area and the area to be cut can be surely determined with reference to the identification mark included in the read image information.

(15) In (12) to (14), in image formation of the image forming device, adjustment is performed to move the abnormality to the area to be cut by moving the image forming area in at least one of the main scanning direction and the sub scanning direction in the paper sheet based on control information for performing the adjustment to move the abnormality to the area to be cut by moving the image forming area in at least one of the main scanning direction and the sub scanning direction in the paper sheet. Accordingly, the adjustment is performed to move the abnormality to the area to be cut by moving the image forming area in at least one of the main scanning direction and the sub scanning direction in the paper sheet. As a result, since the abnormality in the area to be cut is not included in the printed matter by being cut off in post processing, it is possible to avoid finally making a defective printed matter and prevent downtime in image formation.

(16) In (12) to (15), adjustment is performed to move the abnormality to the area to be cut by moving the position of the paper sheet at the time when the image is formed by the image forming device in the main scanning direction. As a result, since the abnormality in the area to be cut is not included in the printed matter by being cut off in post processing, it is possible to avoid finally making a defective printed matter and prevent downtime in image formation.

(17) In (12) to (16), adjustment is performed to move the abnormality to the area to be cut by moving a timing when the image is formed on the paper sheet by the image forming device in the sub scanning direction based on the control information. As a result, since the abnormality in the area to be cut is not included in the printed matter by being cut off in post processing, it is possible to avoid finally making a defective printed matter and prevent downtime in image formation.

(18) In (12) to (17), in a case where the adjustment is performed, a position and a direction of an image to be formed are corrected based on the adjustment. As a result, an image from which the abnormality is removed is formed in the image area, and the abnormality in the area to be cut is not included in the printed matter by being cut off in post processing. Therefore, it is possible to avoid finally making a defective printed matter and prevent downtime in image formation.

(19) In (12) to (18), in a case where the adjustment has been performed, by maintaining the adjusted state before next adjustment, it is possible to avoid a defective printed matter and prevent downtime in image formation.

(20) An image forming system reflecting an aspect of the present invention includes the image forming device in (12) to (19) and a cutting device that cuts an area to be cut of a paper sheet on which an image is formed by an image forming device according to adjustment. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation.

(21) A control program reflecting an aspect of the present invention determines whether an abnormality occurs in an image firmed on a paper sheet with reference to image forming information and read image information, and generates control information to adjust positions of an image forming area and an area to be cut so as to move the abnormality to the area to be cut in a case where the abnormality has been detected in the image forming area and notifies an image forming device of the control information. Accordingly, the image forming device that has received the notification moves the abnormality to the area to be cut by adjusting the positions of the image forming area and the area to be cut according to the notification. As a result, even when the abnormalities on the paper sheet caused when the image is formed continuously occur, the abnormality moves from the image forming area to the area to be cut, and the abnormality in the area to be cut is not included in the printed matter by being cut off in post processing. Therefore, it is possible to avoid finally making a defective printed matter and prevent downtime in image formation.

Although embodiments of the present invention have been described and illustrated in detail, the disclosed embodiments are made for purposes of illustration and example only and not limitation. The scope of the present invention should be interpreted by terms of the appended claims.

What is claimed is:

1. A control device, comprising:
at least one controller comprising a hardware processor that:
receives image forming information including information showing an area to be cut in post processing provided in a paper sheet and information regarding an image formed in an image forming area, and read image information generated by a reading device reading an image formed on the paper sheet, and
detects an abnormality in an image formed on the paper sheet based on a comparison of the image forming information and the read image information;
wherein, when an abnormality is detected in the image forming area, the hardware processor generates control information for adjusting positions of the image forming area and the area to be cut in post processing such that the abnormality is included in the area to be cut, and
transmits the generated control information to an image forming device.

2. The control device according to claim 1, wherein the image forming information further includes post processing information showing that post processing comprising at least one of punching and stapling is performed by associating with positions on the paper sheet, and
the area to be cut includes the post processing position and an area near the post processing position.

3. The control device according to claim 1, wherein the hardware processor determines whether the positions of the image forming area and the area to be cut are adjustable, such that the abnormality is included in the area to be cut, and
if determined as adjustable by the hardware processor, transmitting the control information to the image forming device to make the image forming device form an image based on information regarding an image generated in the image forming area and the control information.

4. The control device according to claim 1, wherein an image of an identification mark for distinguishing the image forming area and the area to be cut by the image forming device is formed on the paper sheet, and
the hardware processor specifies the image forming area and the area to be cut included in the read image information with reference to the identification mark included in the read image information.

5. The control device according to claim 1, wherein in a case where it is assumed that a paper sheet conveying direction be a sub scanning direction and a direction perpendicular to the sub scanning direction on the paper sheet be a main scanning direction when the image is formed by the image forming device,
the hardware processor generates control information to perform adjustment so as to move the abnormality to the area to be cut by moving an image forming area in at least one of the main scanning direction and the sub scanning direction in the paper sheet and the at least one controller notifies the image forming device of the control information.

6. The control device according to claim 1, wherein in a case where it is assumed that a paper sheet conveying direction be a sub scanning direction and a direction perpendicular to the sub scanning direction on the paper sheet be a main scanning direction when the image is formed by the image forming device,
the hardware processor generates control information to perform adjustment so as to move the abnormality to the area to be cut by moving a position of the paper sheet at the time when the image is formed by the image forming device in the main scanning direction and the at least one controller notifies the image forming device of the control information.

7. The control device according to claim 1, wherein in a case where it is assumed that a paper sheet conveying direction be a sub scanning direction and a direction perpendicular to the sub scanning direction on the paper sheet be a main scanning direction when the image is formed by the image forming device,
the hardware processor generates control information to perform adjustment so as to move the abnormality to the area to be cut by moving a timing to form an image on the paper sheet by the image forming device in the sub scanning direction and the at least one controller notifies the image forming device of the control information.

8. The control device according to claim 1, wherein in a case where the abnormalities are detected at the same coordinates in the image forming device before and after adjustment of positions of an image area and the paper sheet, the at least one controller informs that the abnormality is caused by a mechanical factor of the image forming device.

9. The control device according to claim 1, wherein in a case where the abnormalities are detected at the same coordinates in the reading device before and after adjustment of positions of an image area and the paper sheet, the at least one controller informs that the abnormality is caused by a reading failure of the reading device.

10. The control device according to claim 1, wherein in a case where the abnormalities are detected at the same coordinates in an image area before and after adjustment of positions of the image area and the paper sheet, the at least one controller informs that the abnormality is caused by a factor in image processing or an image forming process.

11. A reading device that generates read image information by reading an image formed on a paper sheet, the reading device comprising:
the control device according to claim 1.

12. An image forming device that provides an area to be cut in a paper sheet and forms an image in an image forming area, the image forming device comprising:
a reading device that reads the image formed on the paper sheet and generates read image information; and
the control device according to claim 1.

13. The image forming device according to claim 12, wherein the hardware processor determines whether the positions of the image forming area and the area to be cut are adjustable, such that the abnormality is included in the area to be cut, and if determined as adjustable by the hardware processor, the control device transmits the control information to the image forming device to make the image forming device form an image based on information regarding an image generated in the image forming area and the control information.

14. The image forming device according to claim 12, wherein an image of an identification mark for distinguishing the image forming area and the area to be cut is formed on the paper sheet.

15. The image forming device according to claim 12, wherein in a case where it is assumed that a paper sheet conveying direction be a sub scanning direction and a direction perpendicular to the sub scanning direction on the paper sheet be a main scanning direction when the image is formed by the image forming device, adjustment is performed to move the abnormality to the area to be cut by moving the image forming area in at least one of a main scanning direction and a sub scanning direction in the paper sheet based on the control information.

16. The image forming device according to claim 12, wherein in a case where it is assumed that a paper sheet conveying direction be a sub scanning direction and a direction perpendicular to the sub scanning direction on the paper sheet be a main scanning direction when the image is formed by the image forming device, adjustment is performed to move the abnormality to the area to be cut by moving a position of the paper sheet at the time when the image is formed by the image forming device in the main scanning direction based on the control information.

17. The image forming device according to claim 12, wherein in a case where it is assumed that a paper sheet conveying direction be a sub scanning direction and a direction perpendicular to the sub scanning direction on the paper sheet be a main scanning direction when the image is formed by the image forming device, adjustment is performed to move the abnormality to the area to be cut by moving a timing to form an image on the paper sheet in the sub scanning direction by the image forming device based on the control information.

18. The image forming device according to claim 12, wherein in a case where the adjustment is performed, a position and a direction of an image to be formed are corrected based on the adjustment.

19. The image forming device according to claim 12, wherein in a case where the adjustment has been performed, the adjusted state is maintained before next adjustment.

20. An image forming system comprising:

the image forming device according to claim 12 that adjusts positions of an image forming area and an area to be cut so as to move an abnormality to the area to be cut in a case where the abnormality is detected in the image forming area when an image is formed in the image forming area while providing the area to be cut in a paper sheet; and a cutting device that cuts the area to be cut of the paper sheet on which the image is formed by the image forming device according to adjustment.

21. A non-transitory recording medium storing a computer readable control program for a control device, the control program causing a computer of the control device to:

receive image forming information including information showing an area to be cut in post processing provided in a paper sheet and information regarding an image formed in an image forming area, and read image information generated by a reading device reading an image formed on the paper sheet; and detect an abnormality in an image formed on the paper sheet based on a comparison of the image forming information and the read image information;

wherein when an abnormality is detected in the image forming area by the detector, the control program generates control information for adjusting positions of the image forming area and the area to be cut in post processing such that the abnormality is included in the area to be cut.

* * * * *